(12) United States Patent
Yachia et al.

(10) Patent No.: US 7,654,950 B2  
(45) Date of Patent: Feb. 2, 2010

(54) IMPLANTABLE DEVICE WHICH IS FREELY MOVABLE IN A BODY CAVITY

(75) Inventors: Daniel Yachia, Herzliya (IL); Eran Hirszowicz, Ramat Gan (IL)

(73) Assignee: Innoventions (Israel) Ltd., Caesarea (IL)

( * ) Notice: Subject to any disclaimer, the term of this patent is extended or adjusted under 35 U.S.C. 154(b) by 534 days.

(21) Appl. No.: 10/533,640

(22) PCT Filed: Nov. 4, 2003

(86) PCT No.: PCT/IL03/00915

§ 371 (c)(1),
(2), (4) Date: Nov. 15, 2005

(87) PCT Pub. No.: WO2004/041124

PCT Pub. Date: May 21, 2004

(65) Prior Publication Data

US 2006/0155163 A1 Jul. 13, 2006

(30) Foreign Application Priority Data

Nov. 4, 2002 (IL) .................................... 152630

(51) Int. Cl.
*A61F 2/00* (2006.01)
(52) U.S. Cl. ...................................... 600/29

(58) Field of Classification Search ............. 600/29–32; 128/DIG. 25, 899
See application file for complete search history.

(56) References Cited

U.S. PATENT DOCUMENTS

| 4,925,446 | A  | 5/1990  | Garay et al.   |
|-----------|----|---------|----------------|
| 5,030,199 | A  | 7/1991  | Barwick et al. |
| 5,188,109 | A  | 2/1993  | Saito          |
| 5,234,409 | A  | 8/1993  | Goldberg et al.|
| 5,579,781 | A  | 12/1996 | Cooke          |
| 5,604,531 | A  | 2/1997  | Iddan et al.   |
| 6,293,923 | B1 | 9/2001  | Yachia et al.  |
| 6,398,718 | B1 | 6/2002  | Yachia et al.  |
| 2002/0082551 | A1 | 6/2002 | Yachia et al. |
| 2002/0151923 | A1 | 10/2002 | Holzer        |

FOREIGN PATENT DOCUMENTS

WO WO 00/54701 A1 9/2000
WO WO 00/54702 A1 9/2000

*Primary Examiner*—John P Lacyk
(74) *Attorney, Agent, or Firm*—The Nath Law Group; Susanne M. Hopkins; Derek Richmond

(57) ABSTRACT

An implantable medical device (10) for insertion into a body cavity. The device comprises an expandable balloon having a torroidal shape defining a hole (80), and an insert (82) configured to be received and secured in the hole. The device may be used in a method for treating urinary incompetence, a method for releasing a substance in the body, a method for monitoring a body cavity, or a method for imaging a body cavity.

36 Claims, 13 Drawing Sheets

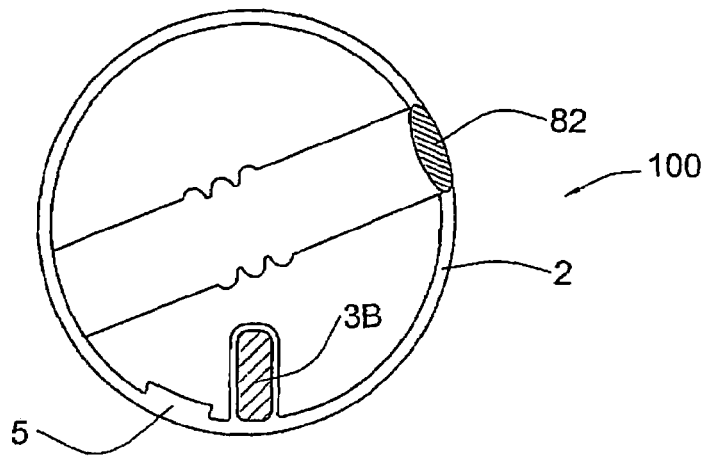
FIG. 1C
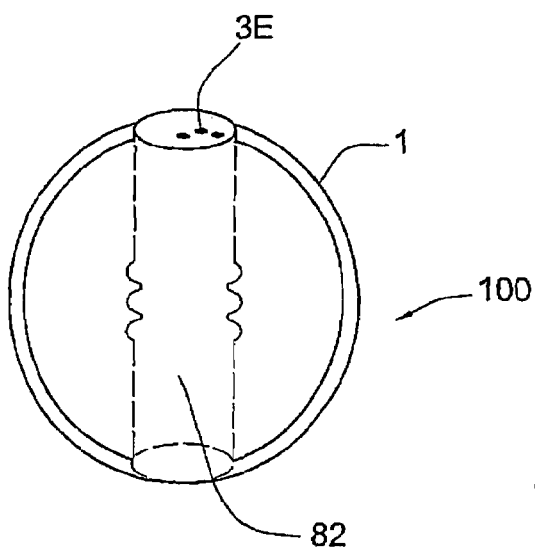
FIG. 1D
FIG. 1E
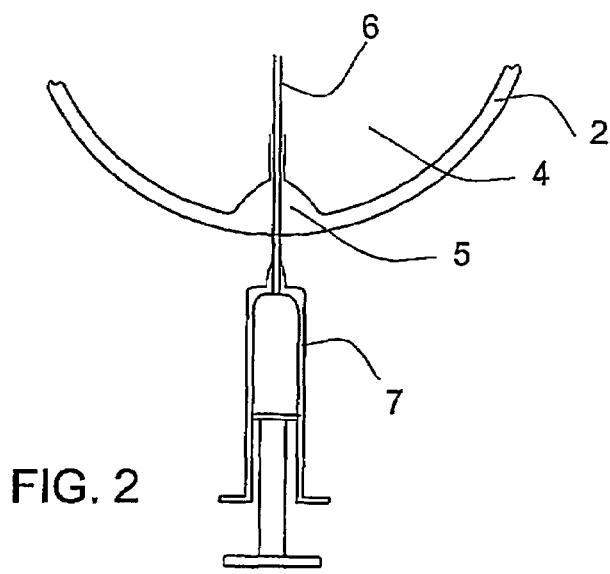
FIG. 2

IMPLANTABLE DEVICE WHICH IS FREELY MOVABLE IN A BODY CAVITY

FIELD OF THE INVENTION

The invention is in the field of implantable medical devices.

BACKGROUND OF THE INVENTION

There are many instances when it is desirable to insert an implantable device into a body cavity such as the urinary bladder or a digestive tract disorder. Such disorders include infections, tumors, or dysfunction. In the case of the urinary bladder, urinary incontinence is also a serious problem. In the following paragraphs these disorders are considered in reference to the urinary tract.

Urinary Incontinence

Urinary incontinence mostly affects women (approximately 10 million in the U.S.A. alone) primarily after childbirth or due to old age. In men, urinary incontinence often occurs as a complication of surgery or old age (approximately 3 million in the U.S.A.).

Incontinence has serious economic, health, social and psychological consequences. Its estimated cost to the health system in the United States in 1993 was US $16 billion. It leads to chronic and severe skin irritation in the genital area, an increase in urinary infections and urosepsis. Fear of incontinence and odors in public cause incontinent people to severely restrict their social activities. The impact on the mental health of the affected people may be even more devastating than the social and health consequences. They suffer severe embarrassment, loss of self-esteem, depression and anxiety.

Urinary incontinence can be divided into 4 groups:

Stress Incontinence—is the involuntary release of urine due to a sudden increase in the intraabdominal pressure caused by laughing, sneezing, coughing, running, etc. This is the most common type of incontinence and in women may be the result of childbirth, estrogen deficiency, unsuccessful surgical repairs for incontinence or pelvic irradiation. In men, it often happens after surgery for benign enlargement of the prostate gland or after radical removal of the prostate.

Total Incontinence—is the continuous leak of urine entering the bladder due to failure of the sphincteric muscles.

Urge Incontinence—is involuntary loss of urine due to involuntary bladder contractions. This type of incontinence mostly affects the elderly who leak until they reach a toilet.

Mixed Incontinence—is a combination of stress and urge incontinence. This condition is more common in elderly women than men.

Ideally, treatment of incontinence should provide permanent dryness and is easy to perform.

Pharmacological treatments of bladder dysfunctions are based either on estrogen replacement for treating post-menopausal vaginal and urethral atrophy or on agents affecting the tonus of the bladder muscle. Since affected elderly women suffer from both hormonal deficiency and urge incontinence, both types of agents are usually prescribed simultaneously.

Surgical treatments are based on restoring the anatomical changes causing the incontinence. Although in the short-term most surgical procedures restore continence, the long-term prognosis is usually unsatisfactory. Moreover, surgery entails morbidity and high expenses.

Conservative/behavioral treatments are based on pelvic floor muscle exercises, bladder training, biofeedback, vaginal cones, low-frequency electrostimulation of pelvic floor muscles, intravaginal bladder neck support pessaries, urethral meatus suction cups and intraurethral devices. Conservative treatments are time consuming and require the patients' understanding, cooperation and persistence.

Devices which have been used to obtain almost immediate dryness in incontinent people can be divided into two groups:

(1) Urethral Plugs/Inserts

These comprise a flexible rod having a 14 Ch. (approximately 4.5 mm) diameter and a length adjusted to fit the length of the patient's urethra. The rod has an inflatable balloon on its bladder end and a flange at other end. After insertion of the device, the balloon is inflated in the bladder. The balloon and the flange maintain the device in its proper position within the urethra. The balloon and rod form a mechanical barrier to retain the urine within the bladder. The balloon must be deflated and the device removed and discarded prior to voiding. Such inserts are known in the art, for example, the device known as RELIANCE™ produced by UroMed Corp., U.S.A.

Since inserts are discarded after each voiding and replaced with a new one by the patient, manual dexterity of the patient is required. Insertion of an insert into a female has the risk of pushing vaginal and perineal bacteria into the bladder and insertion of an insert a few times a day increases this risk. The inconvenience of removing and inserting a new device and its costs, in addition to the infection risk, are the major disadvantages of these devices.

(2) Valve Catheters

These comprise a tube with a valve at one end. The bladder end of the device typically has a balloon or flanges for retaining the device in place and a flange at the other end to prevent migration into the bladder. The valve is opened for voiding through the lumen of the catheter with the help of an external magnet. The tube typically has a 18 Ch. (6 mm.) to 20 Ch. (approximately 7 mm) diameter and a length adjusted to fit the patient's urethra. For male incontinence, an active intraurethral Foley-type catheter is used. This device has a retaining balloon at its bladder end and another smaller balloon under the prostate for fixing the device in place. The magnet activated valve is situated at the end of the device near the distal end of the urethra. Active inserts are typically left indwelling up to 4 weeks and are then replaced. Examples of such catheters are disclosed in U.S. Pat. Nos. 5,030,199 and 5,234,409.

Valve catheters are more convenient for the patient than the inserts. However, in females they cause ascending infection because they connect the bladder with the vulva which is rich in pathogenic bacteria, expecially *Escherichia Coli*. Even with continuous use of antibiotics, infection is unpreventable in the majority of cases.

During prolonged use of catheters or inserts in female patients, a relaxation of the urethra occurs and the patients may start to leak around the device. Unfortunately valve catheters and inserts are unavailable in increasing diameters.

A significant disadvantage of both the inserts and the valve catheters is the discomfort felt by the patient especially when sitting and during sexual intercourse (felt by the patient and the partner). The present invention therefore provides a device for the treatment of urinary incontinence in which the disadvantages of the prior art devices are substantially reduced or eliminated.

Urinary Tract Infections

Nearly half of all women experience urinary tract infection (UTI) at some point in their lifetime aid most of these infections are confined to the bladder. Isolated UTIs can be treated by short and effective antibiotic treatment. However, recurrent UTIs often occur ill women due to antibiotic resistant bacteria. In this case complicated infections often exhibit multidrug resistance and necessitate longer antimicrobial drug administrations.

Treatment of UTI often requires urinary levels of antimicrobial drugs that are several hundred times greater than those allowable in the blood. Many antibacterials cannot be used in UTI because, when taken orally or intravenously, they do not attain the required concentration in the urine, without exceeding the allowable limit in the blood. It would therefore be desirable to be able to continuously introduce antimicrobial drugs continuously and directly into the bladder.

Bladder Tumors

Even after resection, bladder tumors may not only recur but may also invade deeper in the bladder wall. Due to the heterogenity of these tumors (from low-grade tumors showing a benign course to highly malignant high-grade tumors), there does not exist a single approach to the surveillance and treatment of these tumors. Intravesical drug therapies are often used for reducing tumor recurrence. In this approach, an immunotherapeutic or chemotherapeutic agent is inserted into the bladder through a catheter. This treatment is typically repeated once a week for 6 weeks and then once a month for a period of 6-1.2 months. However, periodic treatment has not been established as being effective in altering the progression of the tumor. Continuous local treatment with chemotherapeutic or radioactive materials may treat or prevent not only superficial tumors but also deep tumors as well. It would therefore be desirable to be able to introduce antitumoral drugs continuously and directly into the bladder.

Bladder Dysfunction

During filling, the bladder muscle relaxes for keeping the intravesical pressure low while it contracts for voiding. Certain diseases such as spinal cord injuries, diabetes, multiple sclerosis, or hormonal changes after menopause or old age in both sexes may cause a hypo contractility or, paradoxically, hyper contractility of the muscle. In atonic bladder, pharmacological treatment is not very effective. In hyperreflexic bladder, drugs for relaxing the bladder cause constipation and mouth dryness and are therefore not tolerated well by the patients.

Diagnosis of bladder dysfunction requires continuously monitoring various bladder parameters during filling and/or voiding. These measurements usually are made by inserting a catheter connected to a measuring device into the bladder. This is done, for example, in uroflowmetry (measurement of urinary flow rate) which is non-invasive, simple and inexpensive. However, its sensitivity and specificity are low. Cystometry is an invasive technique for measuring bladder capacity, compliance and muscle tonus. Pressure-flow study is an invasive and costly test for distinguishing patients with low urinary flow due to obstruction or bladder antonia, from those with high intravesical pressure and high urinary flow. It is therefore a need in the art for a simple and inexpensive technique for intravesicular monitoring.

In the diagnostic procedure known as "urodynamics", the bladder is filled through a catheter, and the response of the bladder is monitored. Available 24 hour urodynamic monitors have catheters or wires passing through the urethra, connecting sensors inserted into the bladder to a recorder. The connecting wires and catheters inadvertently introduce pathogenic bacteria from the genital areas into the bladder. It is therefore desirable to be able to monitor bladder function over several cycles of filling and voiding without the need for such wires or catheters.

Diagnosis of some intravesical pathological conditions often involves inserting an endoscope into the bladder and optically scanning the bladder walls. In cases of bleeding in the ureters or the kidneys, the observation of blood coming through the ureteral orifices allows determination of the origin of the bleeding. However, if the bleeding has temporarily stopped at the time of the examination, or if the blood concentration in the urine is insufficient to make the urine red or pink, endoscopy is of little value in reaching a diagnosis. In such cases more invasive procedures are performed in order to enter the upper urinary tract. It is therefore desirable to be able to monitor the bladder over long periods of time.

Bladder shape during filling and its contraction during voiding is important for the diagnosis of certain bladder pathologies. These functions can be followed in fluoroscopy and by sonography. These techniques however are not accurate and cannot be used for monitoring changes in bladder shape over long periods of time. It would therefore be desirable to be able to continuously image the bladder interior over long periods of time.

U.S. Pat. No. 6,293,923 to Yachia et al., discloses a balloon for insertion in the urinary bladder for treatment in order to treat or monitor the bladder. U.S. Pat. No. 4,925,446 discloses a balloon for insertion into the stomach.

SUMMARY OF THE INVENTION

The present invention provides a medical device for implanting in a body cavity such as a urinary bladder or a digestive tract organ. The device comprises a torroidal shaped balloon defining a central hole. The device further includes an insert configured to be received and retained in the hole. The balloon may be filled and compressed prior to insertion of the device into the body cavity and then allowed to expand after insertion in the bladder. Alternatively, the balloon may be filled after insertion so as to expand in the bladder.

The invention may be used for the intermittent sealing of the urinary bladder outlet and the prevention of involuntary urine leakage. Sealing the urinary bladder outlet involves lodging the device in the outlet so as to seal it. Unsealing the outlet to allow voiding of the bladder involves dislodging the device from the outlet.

The invention may also be used for such purposes as for example, delivery of drugs to the body cavity, imaging the body cavity, and measuring parameters of the cavity such as the pressure of the fluid in the cavity. When used for such purposes, the device may be, for example, immobilized in a specific location in the cavity freely floating in the urine in the cavity fluid, etc.

The invention is entirely confined to the cavity and has no parts extending out of the cavity. As will become apparent in the description below, the device is easily inserted and removed. It may be left in the body for prolonged periods of time without encrusting or causing infections and may be displaced within the body at will using a hand held magnet. The invention is comfortable for the patient and does not interfere with the daily activities of the patient including sitting, jogging, riding, or sexual intercourse.

Thus, in its first aspect, the invention provides an implantable medical device for insertion into a body cavity, comprising an expandable balloon having a wall and a lumen and having a torroidal shape defining a hole, and an insert configured to be received and secured in the hole.

Thus, in its second aspect, the invention provides a system for treating a body cavity of an individual, the system comprising:
(a) a device according to the invention;
(b) an applicator for inserting the device into the body of an individual or for removing the device from the individual's urinary bladder, the applicator fitted at an end thereof with a gripping device for releasably gripping the balloon;
(c) an expanding device for expanding the balloon in the body cavity; and
(d) a magnetizable displacing member for displacing the device within the body cavity.

Thus, in its third aspect, the invention provides a method for treating urinary incontinence in an individual comprising:
(a) inserting a device according to the invention into the individual's urinary bladder;
(b) expanding the balloon in the urinary bladder;
(c) displacing the device into a sealing position for sealing the urinary bladder; and
(d) displacing the balloon within the urinary bladder into an unsealing position for voiding the urinary bladder.

Thus, in its fourth aspect, the invention provides a method for releasing one or more substances into a body cavity of an individual comprising:
(a) loading the one or more substances into the insert of a device according to the invention;
(b) inserting the device into the body cavity;
(c) expanding the balloon in the body cavity; and
(d) displacing the device within the body cavity to a desired location Thus, in its fifth aspect, the invention provides a method for monitoring the interior of a body cavity:
(a) inserting a device according to the invention into the body cavity;
(b) expanding the balloon in the body cavity;
(c) displacing the device within the body cavity to a desired location within the body cavity; and
(d) transmitting signals from one or more of the one or more monitoring devices to a receiver.

Thus, in its sixth aspect, the invention provides a method for imagining the interior of a body cavity comprising:
(a) inserting a balloon according to the invention into the individual's urinary bladder;
(b) expanding the balloon in the urinary bladder;
(c) displacing the balloon within the urinary bladder to a desired location within the urinary bladder; and
(d) transmitting signals from the imaging device to a receiver.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 2 shows a portion of a balloon having a duck-bill valve.

DETAILED DESCRIPTION OF SPECIFIC EMBODIMENTS

Figure 1A:
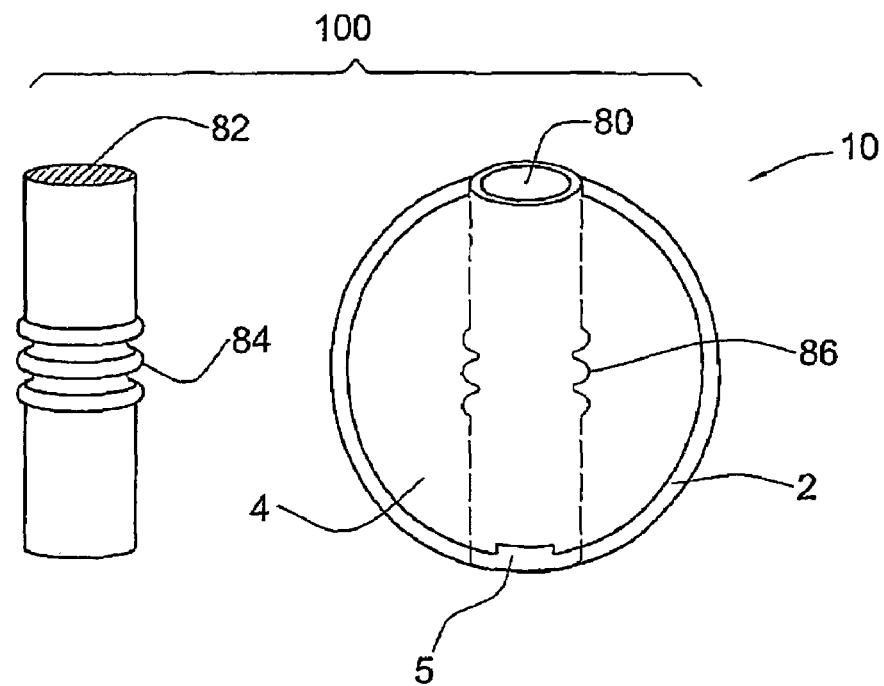
FIG. 1 shows a device in accordance with the invention.
Figure 1B:
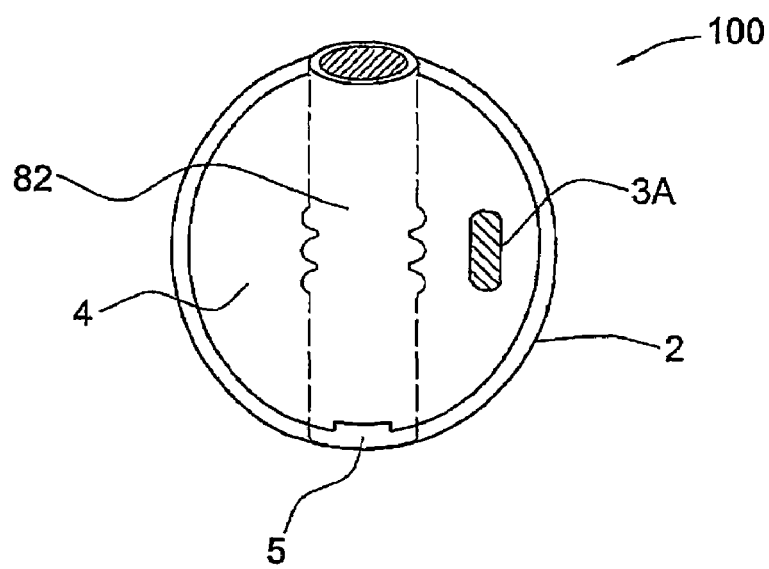

Reference is now made to FIG. 1 which shows a medical device 100 for implantation in a body cavity, in accordance with the invention. The device includes a balloon 1 having a wall 2 made of an elastic biocompatible material enclosing a lumen 4. In accordance with the invention, the balloon, after inflation, has a torroidal shape defining a central hole 80 that is generally cylindrical in shape. The device 100 also includes a generally cylindrically shaped insert 82. The insert 82 is dimensioned to be received in the hole 80, as shown in FIG. 1b. Grooves and ridges 84 on the external surface of the insert 82 may be received in complementary grooves and ridges 86 on the external surface of the wall 2 so as to retain the insert in the hole 80, and to prevent separation of the insert 80 from the balloon 1 during use of the device 100. As described in detail below, the insert 82 is configured to perform any desired function after implantation of the device in the body cavity such as, releasing a substance or substances into the cavity, imaging the cavity, monitoring the cavity, or irradiating the cavity. Also as described in detail below, the device may be used to control release of fluids from the cavity. The devicee The balloon 1 or the insert 82 may further comprise a magnetable portion which may consist for example, of one or more metal particles which may be free in the lumen 3a of the balloon 1 (as in FIG. 1b), attached to the inner surface 3b of the balloon 100 (as in FIG. 1c), embedded in the wall 3c of the balloon 1 (as in FIG. 1d), or attached to the insert 82 (3e) as shown in FIG. 1e. The lumen 4 of balloon 1 may be filled with a biocompatible fluid which may be presterilized such as air, water, saline or an oil such as liquid paraffin.

Figure 3A:
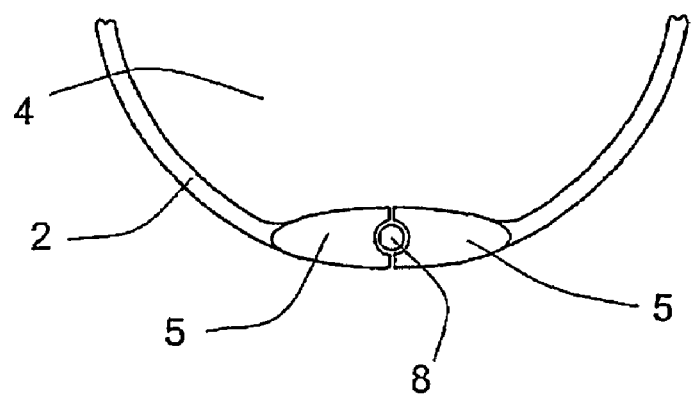
FIG. 3 shows a portion of a balloon having a ball valve.
Figure 3B:
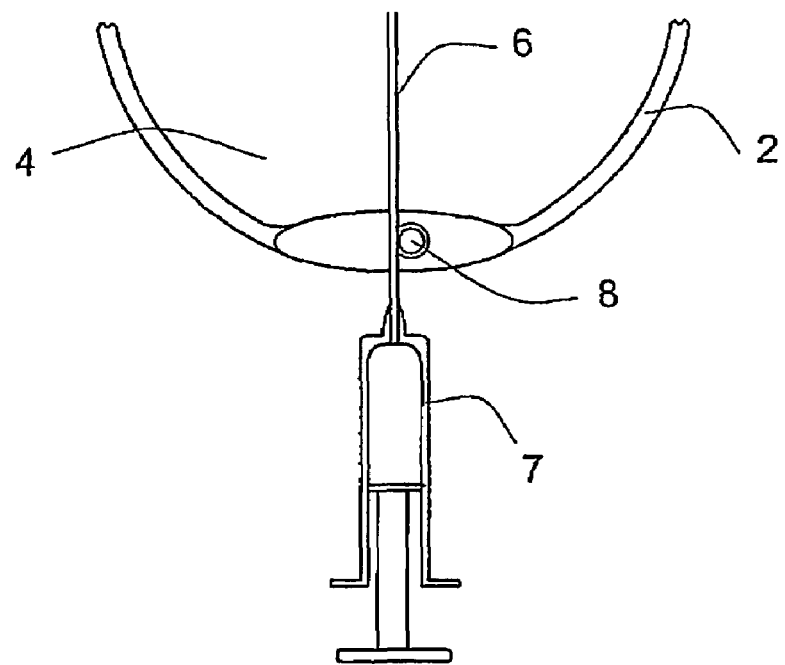

A self-sealing valve 5 in the wall of the balloon is used to fill the balloon. The valve 5 may be for example a duck-bill type valve as shown in FIG. 2 or a ball valve as shown in FIG. 3 in which a ball 8 may be in a sealing position (FIG. 3a) or an unsealing position (FIG. 3c). The canula 6 of a syringe 7 is inserted through the valve 5 into the lumen 4 of the balloon. The fluid injected into the lumen 4 causes the balloon to expand. After filling, the syringe needle 6 is withdrawn, and the valve 5 seals itself. After filling, the balloon may adopt a predetermined shape, for example, a sphere, ellipsoid, or an irregular shape. The inflated inflated balloon may float or sink in the liquid contents of the body cavity.

Figure 4A:
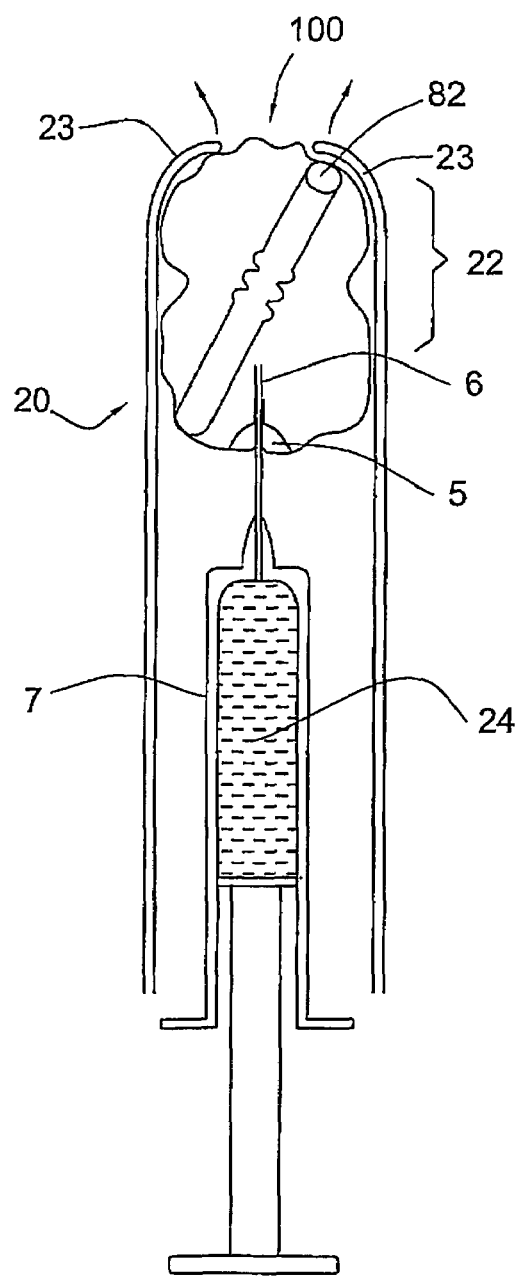
FIG. 4 shows a balloon filled after have been inserted into a body cavity.
Figure 4B:
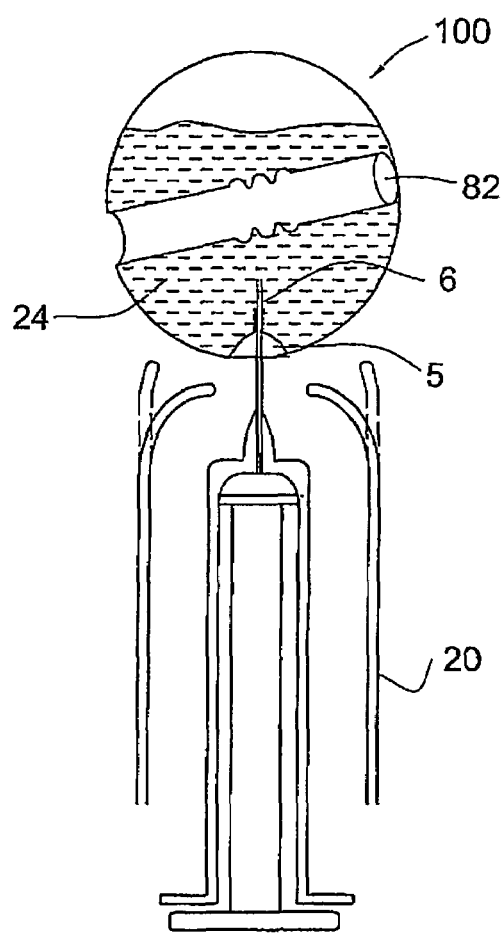
Figure 5A:
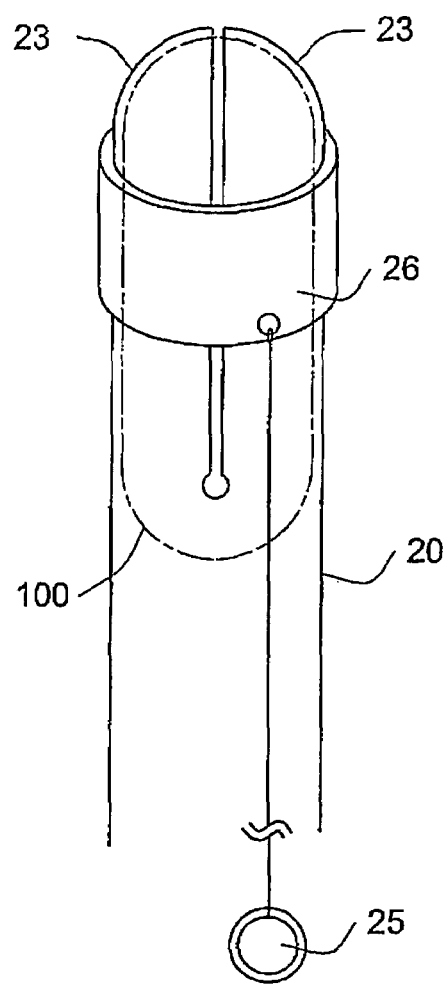
FIG. 5 shows a balloon filled before being inserted into the body cavity.
Figure 5B:
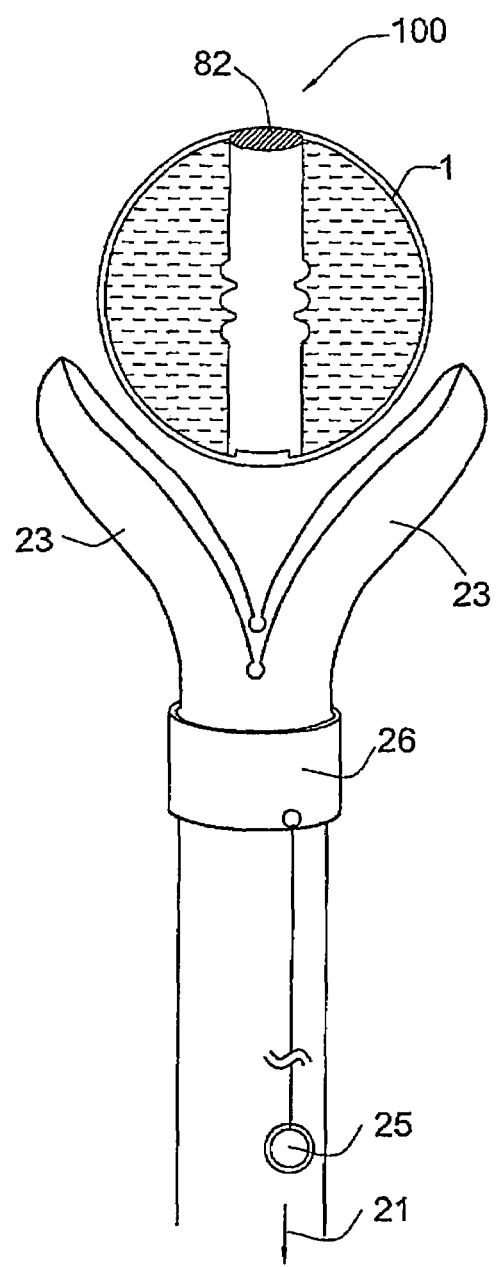

The insert 82 may be inserted into the hole 80 either before the balloon is inflated or afterwards. As shown in FIG. 4, the insert may be inserted into the hole 80 with the balloon 1 deflated, and the device inserted into the cavity by means of an applicator 20 to be described in detail below (FIG. 4a). Following release of the device from the applicator into the body cavity, the balloon 1 then filled with fluid 24 from a syringe 7 (FIG. 4b). Alternatively, as shown in FIG. 5a, the balloon 1 may be filled outside the body and the insert 82 inserted into the hole 80. The balloon 1 is then compressed before being inserted into the cavity by means of applicator 20. The device 100, comprising the pre-filled balloon 1 and the insert 82, is clutched by the flanges 23 which are initially kept closed by constraining sleeve 26 (FIG. 5a). After insertion of the applicator 20 into the body cavity, ring 25 is pulled as indicated by arrow 21 in FIG. 5b to urge the constraining sleeve 26 away from the flanges 23, allowing flanges 23 to open and release the device 100 into the bladder.

Figure 6:
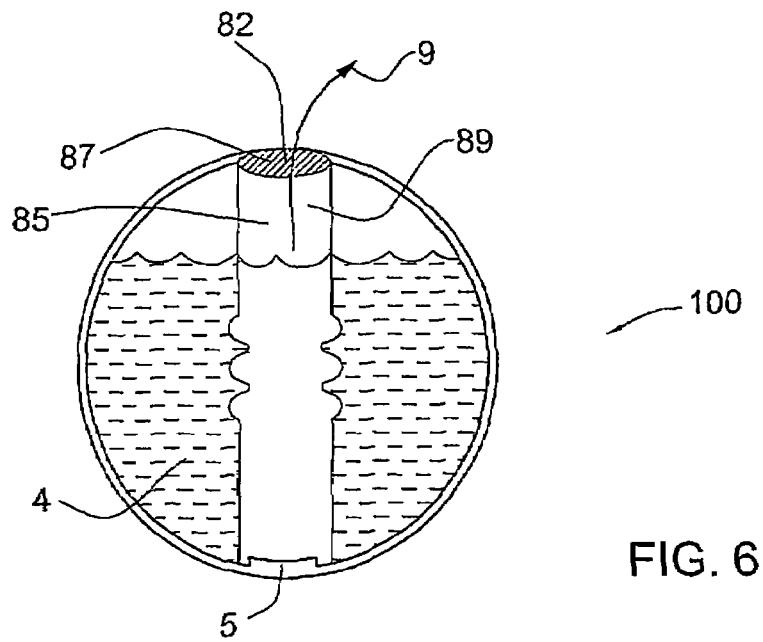
FIG. 6 shows a device having an insert configured to release substances into the body cavity.

FIG. 6 shows the insert 82 constructed so as to have a lumen 82 configured to contain one or more diffusible substances 85. A porous membrane 87 separates the substances 85 from the liquid in the body cavity. The properties of the membrane are selected in order to achieve a desired release rate of the substances 85 into the body cavity, as is known in the art. The substances 85 could be, for example, drags, antibiotics immunoglobulins, or radioactive substances, etc. After insertion of the device 100 into the body cavity, the substances diffuse from the insert 82 into the cavity (arrows 9) in order to achieve a desired effect.

Figure 7:
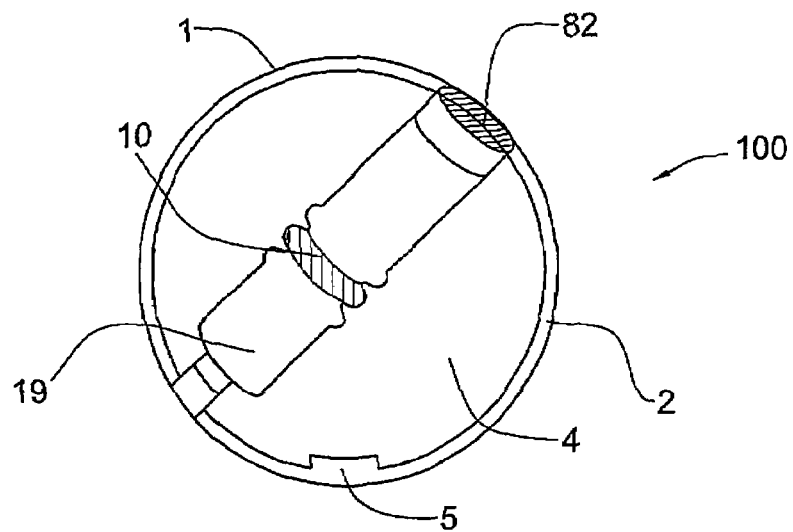
FIG. 7 shows a device comprising a micro-video camera.
Figure 7:
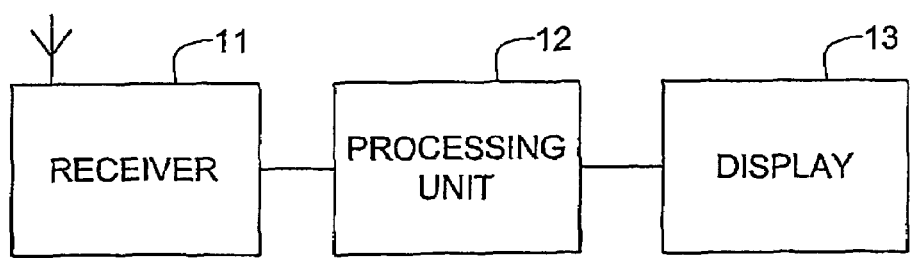

FIG. 7 shows the insert 82 constructed so as to comprise a micro-video camera 19 for imaging the interior of the body cavity. The video camera 19 may have associated with it a transmitter 10 for transmitting images to a remote receiver 11. Such micro-video cameras and transmitters are known in the art, for example, as disclosed in U.S. Pat. Nos. 5,604,531, 5,579,781 and 5,188,109. The receiver 11 may be connected to a processing unit 12 for processing the images, or a display 13 for displaying images.

Figure 8:
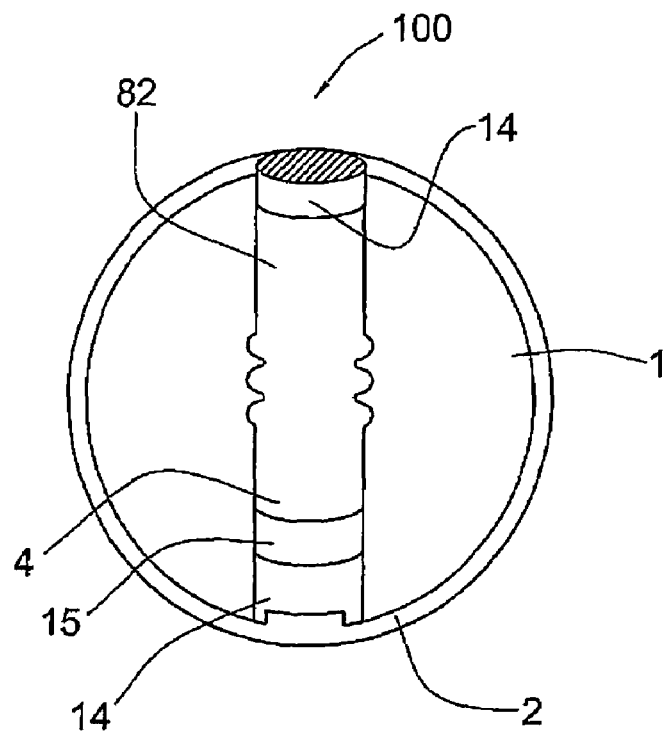
FIG. 8 shows a device comprising devices for measuring parameters of a body cavity.
Figure 8:
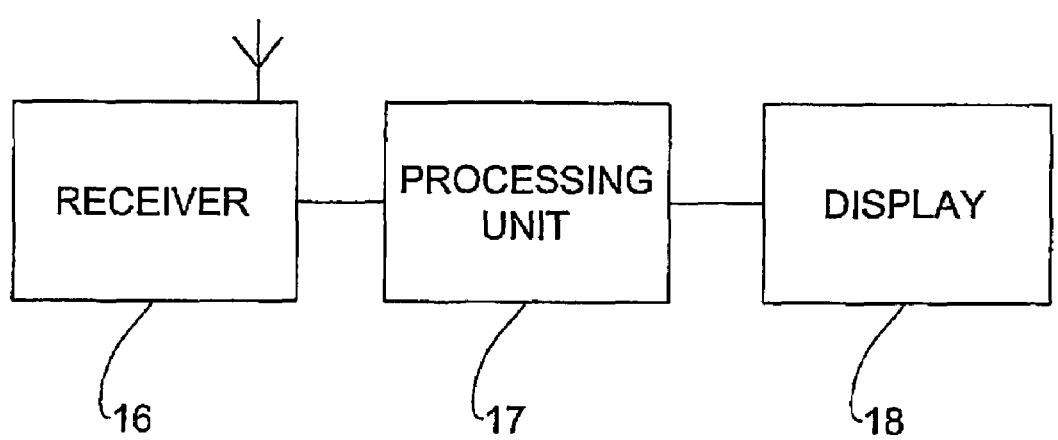

FIG. 8 shows an insert 82 constructed so as to comprise one or more measuring devices 14 for measuring one or more parameters associated with the body cavity, for example, fluid pressure in the cavity, fluid temperature, fluid density, fluid conductivity or fluid composition. The measuring devices 14 may have an associated transmitter 15 for transmitting measurements to a remote receiver 16. The receiver may be connected to a processing unit 17 for processing the measurements or to a display 18 for displaying results. Such measuring devices are known in the art, for example as disclosed in U.S. Pat. Nos. 5,579,781 and 5,188,109.

Figure 9:
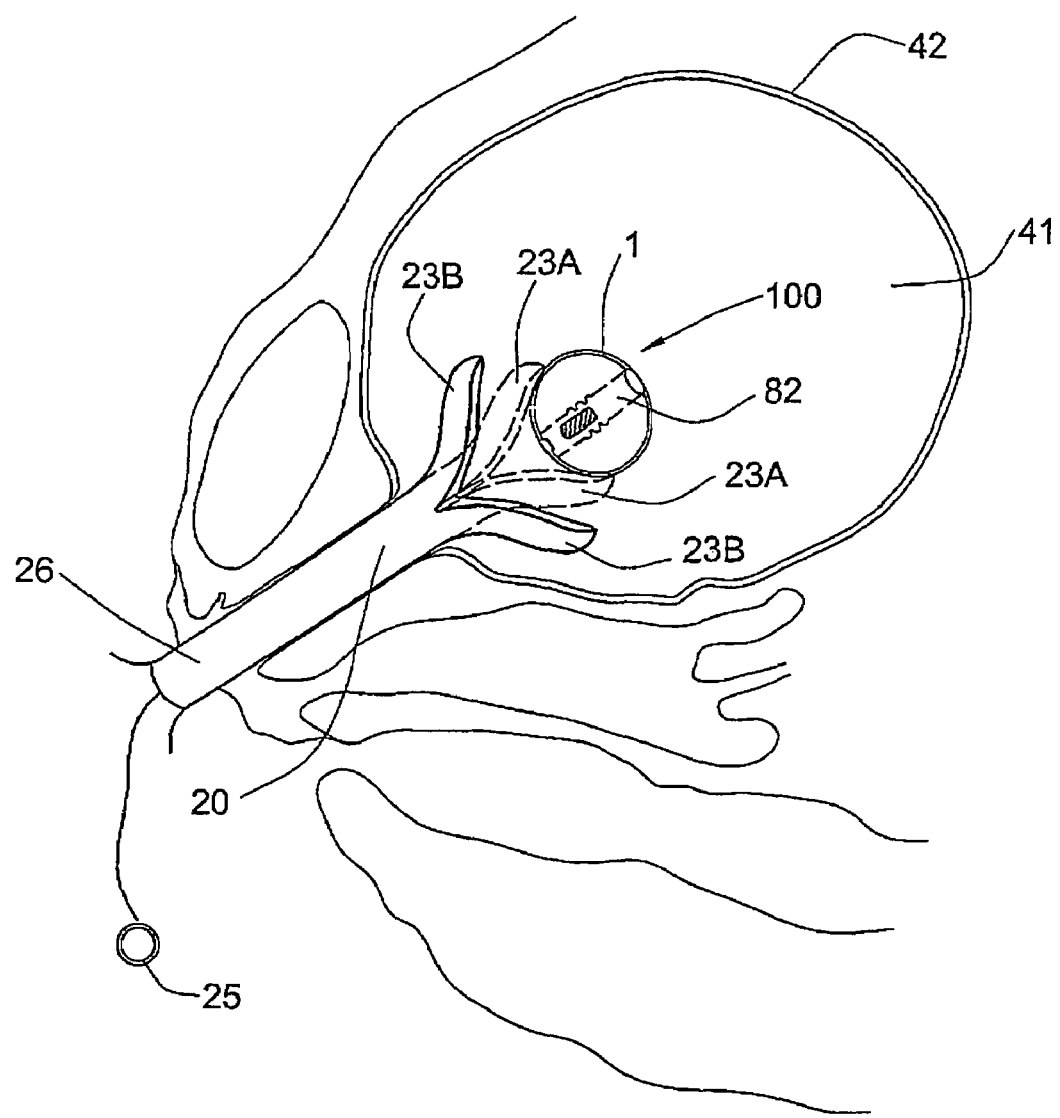
FIG. 9 shows use of an applicator for inserting the device into the urinary bladder of a female individual.
Figure 10:
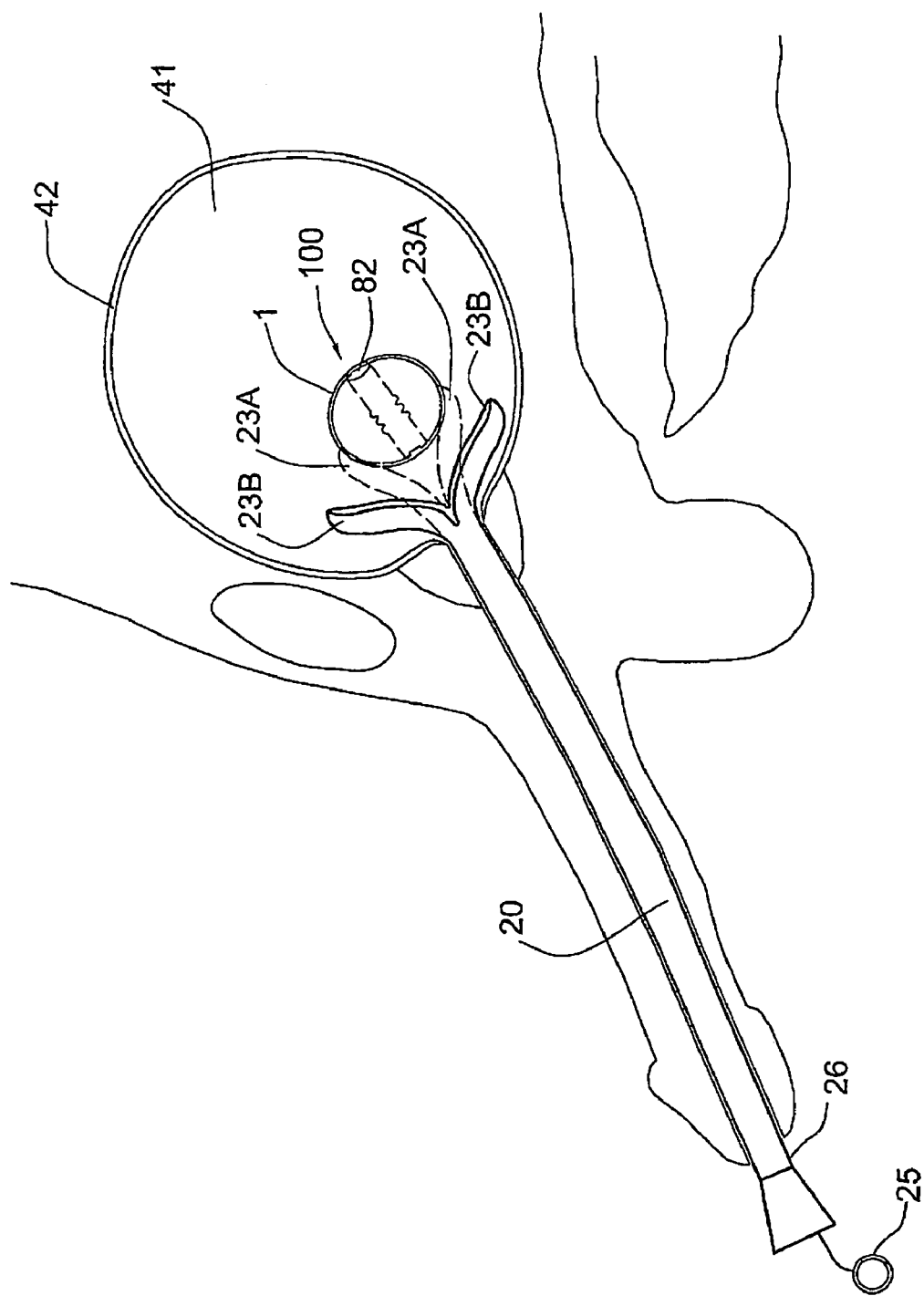
FIG. 10 shows use of an applicator for inserting the device into the urinary bladder of a male individual.

FIG. 9 shows use of an applicator 20 for inserting the device 100 into the lumen 41 of the urinary bladder 42 of a female individual, and FIG. 10 shows use of the applicator 20 inserting the device into the lumen of the urinary bladder 42 of a male individual. In either case the device 100 is initially grasped by the closed flanges 23a at the distal end of the applicator 20 (FIGS. 9a and 10a). The distal end of the applicator-device combination is inserted into the urethra until it reaches the lumen 41 of the bladder 42. The device 100 is then released from the applicator by opening the flanges 23b by puling on ring 25 awhile holding the constraining sleeve 26. The applicator 20 is then removed from the body, leaving the device 100 in the bladder lumen 41.

Figure 11:
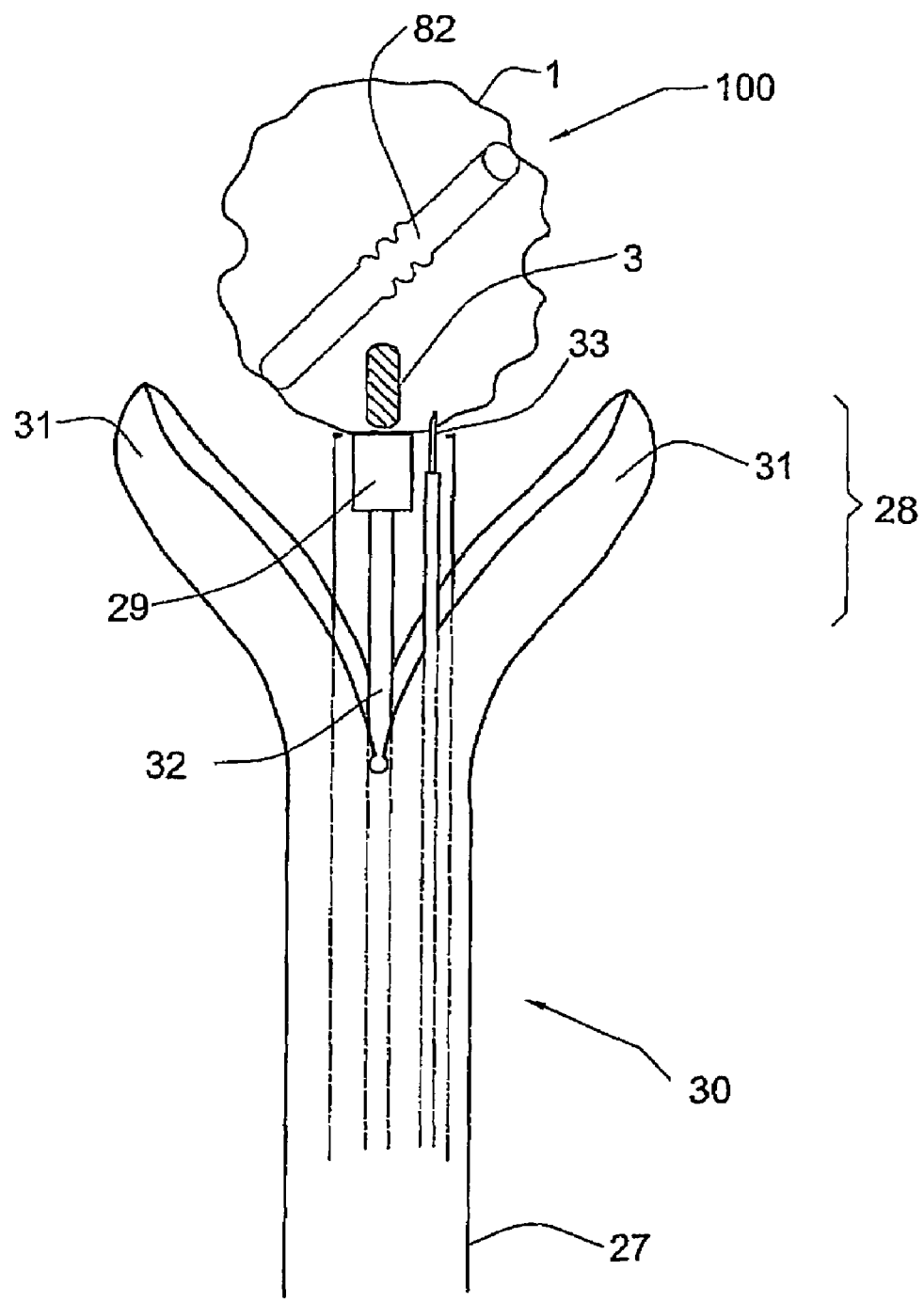
FIG. 11 shows a retrieval device for retrieving the device.

FIG. 11 shows a retrieval device generally designated as 30 for removing the device 100 from the bladder. A catheter 27 has at its distal end 28 a magnetizable portion 29 so as to hold the device 100 at the distal tip 28 by means of the magnetizable particles 3 associated with the device 100.

The retrieval device is inserted into the body cavity. After opening the flanges 31 of the retrieval device, the engaging probe 32, with magnetizable portion 29 in its tip, is inserted into the body cavity so as to engage the magnetizable particle 3 and push the balloon into the lumen of the cavity. The probe 32 is then pulled so as to bring the device into the grip of flanges 31 of the retrieval device. A piercer 33 is inserted into the balloon 1 to drain the fluid contained in its lumen 4 into an attached syringe (not shown) or into the body cavity. The applicator 20 is then withdrawn from the patient together with the device including the deflated balloon 1 and the insert 82.

Figure 12:
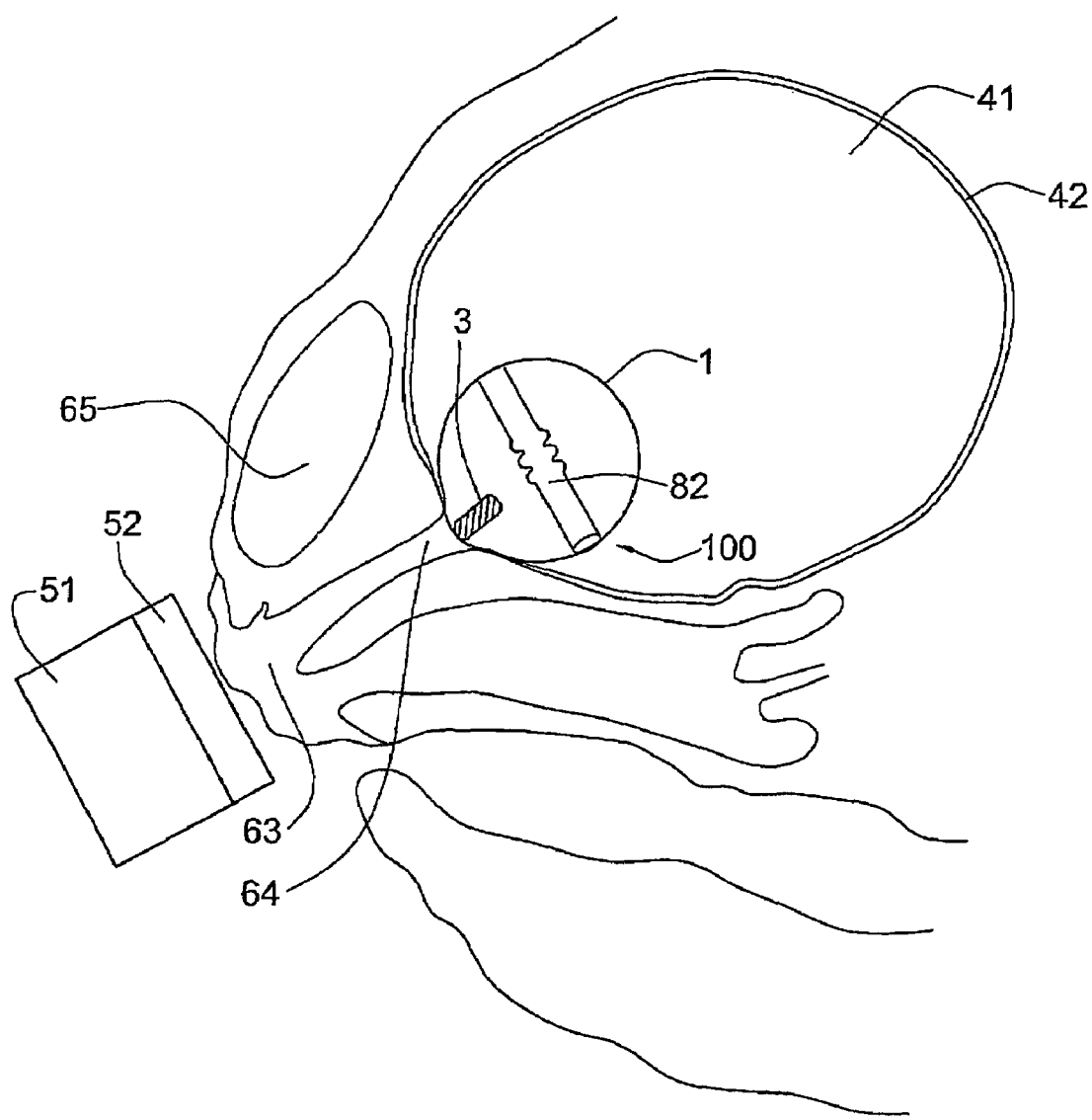
FIG. 12 shows use of a displacing member to displace the device into a sealing position within a urinary bladder.
Figure 13:
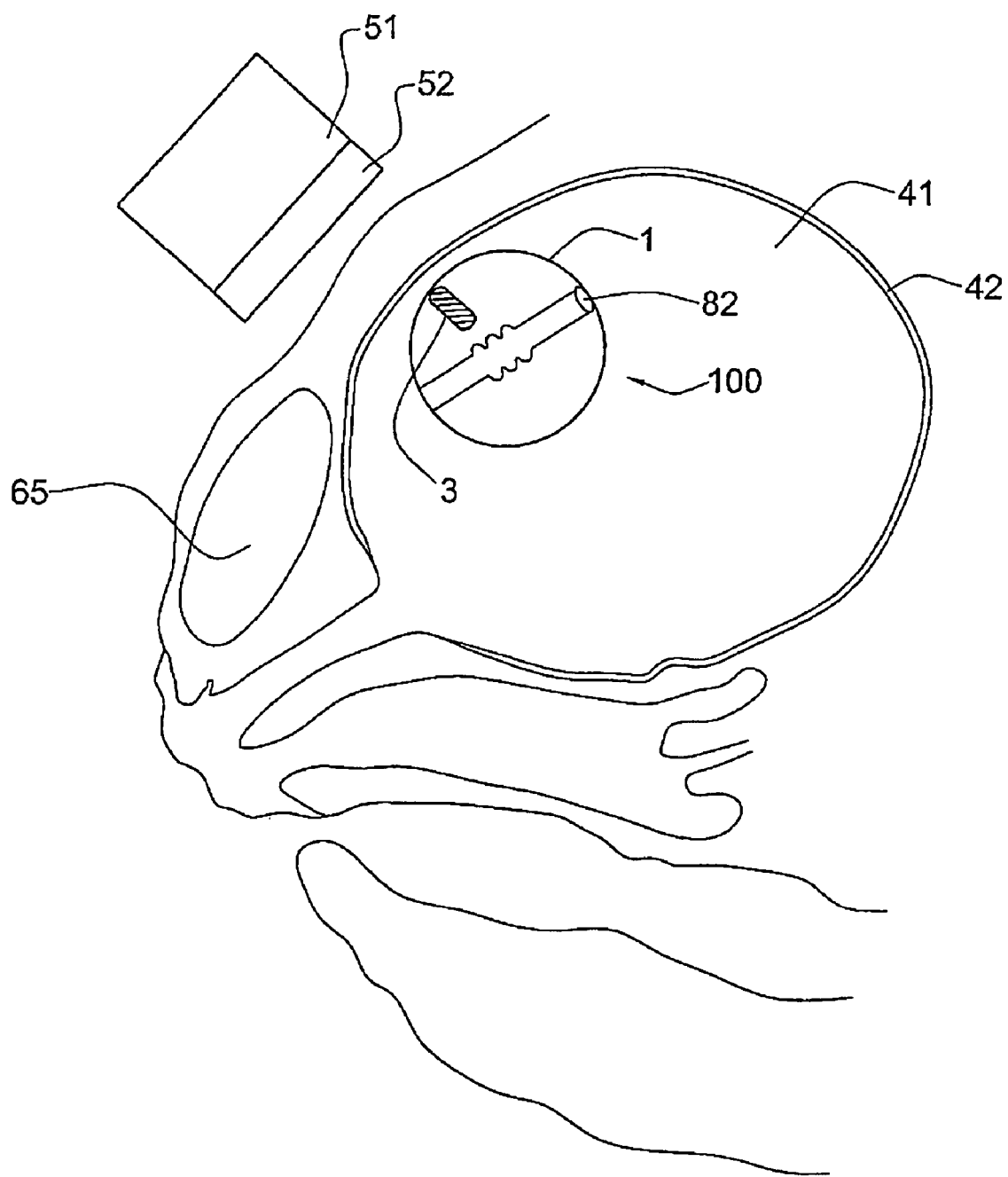
FIG. 13 shows use of a displacing member to displace the device from a sealing position in the urinary bladder.

FIGS. 12 and 13 show use of a displacing member 51 to position the device 100 at a desired location within the lumen 41 of a body cavity. The displacing member 51 is located outside the individual's body and comprises a magnetizable portion 52. The displacing member 51 is placed at a location on the surface of the individual's body so as to draw the device 100 from its initial location to the desired location.

FIG. 12 shows use of the device 100 for sealing the urinary bladder outlet in a female subject. Displacing member 51 is placed over the urethral meatus 63 such that, due to the magnetizable portion 52 associated with the displacing member 51 and the magnetizable portion 3 associated with the device 100, the device is drawn into the bladder outlet 64. The device thus becomes lodged in the outlet and seals it. As the amount of urine in the bladder increases, a hydrostatic pressure is exerted on the device further lodging it in the outlet and reinforcing the seal. The invention is used similarly for sealing the urinary bladder outlet in male subjects.

As seen in FIG. 13, in order to open the urinary bladder for voiding, the magnetic displacing member 51 is placed over the upper edge of the pubic bone 65. Due to the magnetizable portion 3 of the device 100, the device 100 is raised and dislodged from the bladder outlet 64 so as to allow voiding of urine as indicated by arrow 66. After voiding the device 100 is redrawn into the bladder outlet 64 by the displacing member 51 so as to seal the outlet again as shown if FIG. 12.

Figure 14:
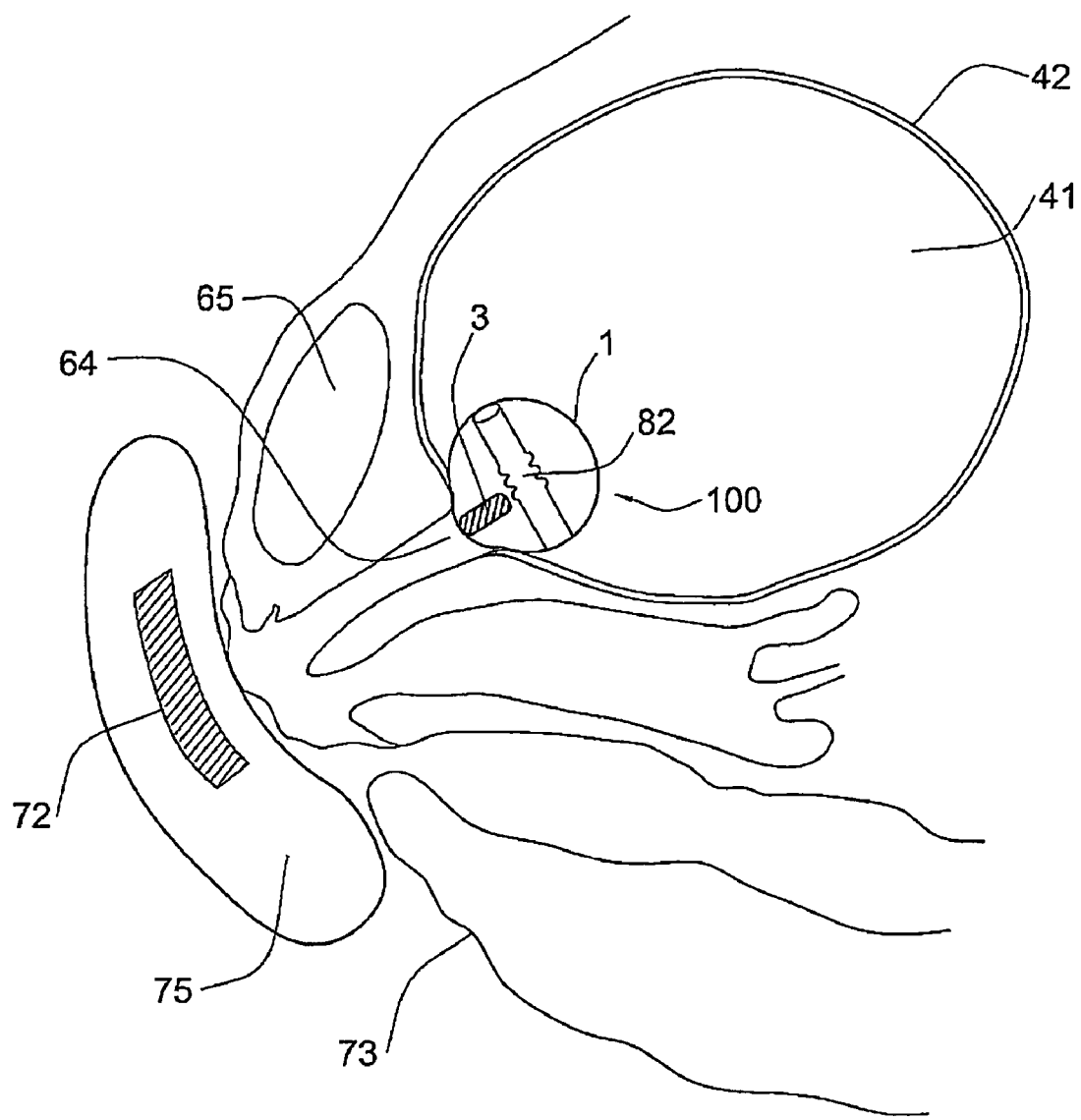
FIG. 14 shows use of an immobilizing member.

FIG. 14 shows use of an immobilizing member 71 comprising a magnetizable portion 72 affixed to the surface 73 of the individual's body so as to maintain the device at a desired location in the lumen 41 of the body cavity 42, which may be for example, a urinary bladder. The magnetizable portion 72 of immobilizing member 71 may be enclosed in a coating 75 so as to form, for example, a hygienic pad. The immobilizing member 71 may be affixed to the surface 73 by means of tape, or by pressure applied to it by the individual's clothing, or may fit in a specially designed pocket in the individual's clothing.

The invention has been described with a certain degree of particularly only for the sale of clarity. However, several variations and modifications in the invention are possible without exceeding the scope and spirit of the invention as defined in the following set of claims.

The invention claimed is:

1. An implantable medical device for insertion into a body cavity, comprising
    an expandable balloon having a torroidal shape defining a passageway and a lumen, the passageway comprising at least one first annular ridge and at least one first annular groove juxtaposed to the first annular ridge, a plane of the first annular ridge and of the annular groove being perpendicular to an axis of the passageway; and
    an insert configured to be received and secured in the passageway, having an external surface comprising insert grooves and insert ridges that are complementary to the first annular groove and first annular ridge.

2. The device according to claim 1, further comprising a magnetizable portion.

3. The device according to claim 2, wherein the magentizable portion comprises one or more magnetizable particles in the lumen of the balloon, attached to a wall of the balloon, or embedded in the wall of the balloon.

4. The device according to claim 2, wherein the magnetizable portion of the balloon comprises one or more magnetizable particles in a lumen of the insert, attached to a wall of the insert, or embedded in a wall of the insert.

5. The device according to claim 1, wherein the body cavity is a urinary bladder or a digestive tract organ.

6. The device according to claim 1, in which the balloon further comprises a self-sealing valve.

7. The device according to claim 1, wherein the device upon expansion of the balloon floats in the body cavity.

8. The device according to claim 1, wherein the device upon expansion of the balloon sinks in the body cavity.

9. The device according to claim 1, wherein the insert is configured to store one or more substances and release them into the body cavity.

10. The device according to claim 9, wherein the one or more substances are stored in a lumen of the insert.

11. The device according to claim 9, wherein a wall of the insert comprises a means for storing one or more substances.

12. The device according to claim 9, wherein one or more of the one or more substances are drugs or antibiotics.

13. The device according to claim 9, wherein one or more of the one or more substances are radioactive substances.

14. The device according to claim 1, wherein the insert comprises a device for imaging the body cavity.

15. The device according to claim 1, wherein the insert comprises one or more devices for monitoring one or more parameters of the body cavity or its contents.

16. The device according to claim 15, wherein one or more of the one or more devices monitors a parameter of the body selected from the group consisting of
fluid pressure;
fluid temperature;
fluid density; and
fluid composition.

17. The device according to claim 14, wherein the insert comprises an imaging transmitter for transmitting signals from the imaging device to a receiver.

18. The device according to claim 15, wherein the insert further comprises a transmitter for transmitting signals from the monitoring device to a receiver.

19. A system for treating a body cavity of an individual, the system comprising:
an implantable medical device for insertion into a body cavity, comprising
an expandable balloon having a torroidal shape defining a passageway and a lumen the passageway comprising at least one first annular ridge and at least one first annular groove juxtaposed to the first annular ridge, a plane of the first annular ridge and of the annular groove being perpendicular to an axis of the passageway; and
an insert configured to be received and secured in the passageway, having an external surface comprising insert grooves and insert ridges that are complementary to the first annular grooves and first annular ridges,
an applicator for inserting the device into the body of an individual or for removing the device from the individual's body cavity, the applicator fitted at an end thereof with a gripping device for releasably gripping the balloon;
an expanding device for expanding the balloon in the body cavity; and
a magnetizable displacing member for displacing the device within the body cavity.

20. The system according to claim 19, further comprising an immobilizing member comprising a magnetizable portion, said immobilizing member being secured onto the individual's body for immobilizing the device at a desired location in the body cavity.

21. The system according to claim 20, wherein the immobilizing member is in the form of a hygienic pad to be placed in the individual's clothing.

22. The system according to claim 19, wherein the gripping device comprises flanges.

23. The system according to claim 19, wherein the gripping device comprises a magnetizable portion.

24. The system according to claim 14, wherein the expanding device comprises an injector for injecting a fluid into the balloon so as to expand the balloon.

25. The system according to claim 19, wherein the expanding device comprises a decompressor for decompressing a balloon so as to expand the balloon.

26. The system according to claim 19, wherein the insert comprises one or more devices for monitoring one or more parameters of the body cavity or its contents, a transmitter for transmitting signals from the monitoring device to a receiver, and a receiver for receiving signals from said transmitter.

27. The system according to claim 26, further comprising one or more components selected from the group consisting of
a processing unit for processing signals received from the receiver;
a display for displaying signals received by the receiver; and
a display for displaying an output produced by a processing unit.

28. The system according to claim 26, for use in monitoring one or more parameters of the body cavity selected from the group consisting of
fluid temperature;
fluid pressure;
fluid density;
fluid conductivity; and
fluid composition.

29. The system according to claim 26, further comprising one or more components selected from the group consisting of
a processing unit for processing signals received from the receiver;
a display for displaying signals received by the receiver; and
a display for displaying an output produced by a processing unit.

30. The system according to claim 26, for use in imaging the body cavity.

31. A method for treating urinary incontinence in an individual comprising:
inserting into the individual's urinary bladder an implantable medical device for insertion into a body cavity, comprising
an expandable balloon having a torroidal shape defining a passageway and a lumen the passageway comprising at least one first annular ridge and at least one first annular groove juxtaposed to the first annular ridge, a plane of the first annular ridge and of the annular groove being perpendicular to an axis of the passageway; and
an insert configured to be received and secured in the passageway, having an external surface comprising insert grooves and insert ridges that are complementary to the first annular grooves and first annular ridges, and
a magnetizable portion;
expanding the balloon in the urinary bladder;
displacing the device into a sealing position for sealing the urinary bladder; and displacing the balloon within the urinary bladder into an unsealing position for voiding the urinary bladder.

32. A method for releasing one or more substances into a body cavity of an individual comprising:
   loading the one or more substances into the insert of a device an expandable balloon having a torroidal shape defining a passageway and a lumen the passageway comprising
      at least one first annular ridge and at least one first annular groove juxtaposed to the first annular ridge, a plane of the first annular ridge and of the annular groove being perpendicular to an axis of the passageway; and
      an insert configured to be received and secured in the passageway, having an external surface comprising insert grooves and insert ridges that are complementary to the first annular grooves and first annular ridges, wherein the insert is configured to store one or more compounds and release them into the body cavity;
   inserting the device into the body cavity;
   expanding the balloon in the body cavity; and
   displacing the device within the body cavity to a desired location.

33. The method of claim 32, wherein one or more of the one or more substances are selected from the group consisting of
   drugs;
   antibiotics; and
   radioactive substances.

34. A method for monitoring the interior of a body cavity:
   inserting into the body cavity an implantable medical device for insertion into a body cavity, comprising
      an expandable balloon having a torroidal shape defining a passageway and a lumen the passageway comprising at least one first annular ridge and at least one first annular groove juxtaposed to the first annular ridge, a plane of the first annular ridge and of the annular groove being perpendicular to an axis of the passageway; and
      an insert configured to be received and secured in the passageway, having an external surface comprising insert grooves and insert ridges that are complementary to the first annular grooves and first annular ridges, wherein the insert comprises a device for imaging the body cavity and a transmitter for transmitting signals from the imaging device to a receiver;
   expanding the balloon in the body cavity;
   displacing the device within the body cavity to a desired location within the body cavity; and
   transmitting signals from one or more of the one or more monitoring devices to a receiver.

35. A method for imagining the interior of a body cavity comprising:
   inserting into the individual's urinary bladder an implantable medical device comprising
      an expandable balloon defining a passageway and a lumen, the passageway comprising at least one first annular ridge and at least one first annular groove juxtaposed to the first annular ridge, a plane of the first annular ridge and of the annular groove being perpendicular to an axis of the passageway; and
      an insert configured to be received and secured in the passageway, and having an external surface comprising insert grooves and insert ridges that are complementary to the first annular grooves and first annular ridges, wherein the insert comprises an imaging device, and a transmitter for transmitting signals from the imaging device to a receiver;
   expanding the balloon in the urinary bladder;
   displacing the balloon within the urinary bladder to a desired location within the urinary bladder; and
   transmitting signals from the imaging device to a receiver.

36. The method of claim 34, further comprising one or more steps selected from the group consisting of
   storing the signals in a computer memory;
   displaying the signals on a display;
   processing the signals in a computer processing unit;
   storing results of the processing in a computer memory; and
   displaying results of the processing on a display.

* * * * *